United States Patent [19]

Herweh et al.

[11] 4,382,134

[45] May 3, 1983

[54] 3-SUBSTITUTED-7-ALKOXY-SPIRO(2H-1-BENZOPYRAN-2,3'-(3H)-NAPHTHO(2,1-B)PYRANS)

[75] Inventors: John E. Herweh, Lancaster; Thomas B. Garrett, Lititz; Alan B. Magnusson, Lancaster, all of Pa.

[73] Assignee: Armstrong World Industries, Inc., Lancaster, Pa.

[21] Appl. No.: 313,732

[22] Filed: Oct. 22, 1981

[51] Int. Cl.$^3$ .................. C08F 234/02; C07D 311/96
[52] U.S. Cl. ..................................... 526/268; 549/344
[58] Field of Search ........................ 549/344; 526/268

[56] References Cited

U.S. PATENT DOCUMENTS

| | | | |
|---|---|---|---|
| 2,978,462 | 4/1961 | Berman et al. | 260/345.2 |
| 3,022,318 | 2/1962 | Berman et al. | 260/345.2 |
| 3,666,525 | 5/1972 | Kimura | 117/36.8 |
| 3,810,762 | 5/1974 | Laridon et al. | 96/48 R |
| 3,810,763 | 5/1974 | Laridon et al. | 96/48 R |
| 3,899,514 | 8/1975 | Baumann et al. | 260/345.2 |
| 3,971,808 | 7/1976 | Baumann et al. | 260/345.2 |
| 4,029,677 | 6/1977 | Baumann et al. | 260/345.2 |
| 4,110,348 | 8/1978 | Baumann et al. | 260/345.2 |
| 4,348,508 | 7/1982 | Herweh et al. | 549/344 |

FOREIGN PATENT DOCUMENTS 10740  5/1980  European Pat. Off. ......... 260/345.2

OTHER PUBLICATIONS

Feichtmayr et al., Liebigs Ann. Chem., 1979(9), 1337–1345.

*Primary Examiner*—Nicky Chan
*Assistant Examiner*—C. Joseph Faraci

[57] ABSTRACT

Substituted spiropyrans particularly suitable for use as precursors to stable pyrylium salts are disclosed.

4 Claims, No Drawings

3-SUBSTITUTED-7-ALKOXY-SPIRO(2H-1-BENZO-PYRAN-2,3'-(3H)-NAPHTHO(2,1-B)PYRANS)

This invention relates to substituted spiropyrans.

More specifically, this invention relates to 3-substituted-7-alkoxy-2,2'spiro (2H-1-benzopyran-2,3'-(3H)-naphtho (2,1-b) pyrans).

Spirobipyrans are of interest as precursors for the UV generation of colored pyrylium salts for use in applications as varied as dosimetry and optical data storage to the formation of non-contact decorative patterns (See S. Maslowski, "High Density Data Storage UV Sensitive Tape," Applied Optics, 13, No. 4, 857 (1974).

The present invention provides a novel type of substituted spiropyrans particularly suitable for use as precursors to stable colored pyrylium salts.

According to this invention there is provided a compound having the formula

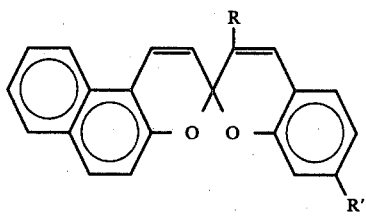

wherein R represents alkylene aryl, aryl, cycloalkyl, or unsaturated alkyl and R' represents alkoxy.

The term "aryl" is used in the specification and claims to signify phenyl or naphthyl, both of which may be unsubstituted or substituted in up to two positions with a substituent selected independently from $C_1$–$C_4$ alkyl, halo or —$NO_2$. "$C_1$—$C_4$ alkyl" is used above to signify a straight or branched alkyl group containing from 1 to 4 carbon atoms and "halo" is used above to signify fluoro, chloro, iodo and bromo.

The term "alkylene aryl" is used in the specification and claims to signify a moiety of the formula M-X—, wherein M represents aryl, as defined above, and X represents a straight or branched alkyl group having from 1 to 3 carbon atoms.

The term "unsaturated alkyl group" is used in the specification and claims to signify a straight or branched alkyl group containing at least 1 carbon-carbon double bond and having from 2 to 12 carbon atoms, with no more than 6 carbon atoms in its longest chain.

The term "cycloalkyl" is used in the specification and claims to signify a cyclic saturated alkyl group having from 3 to 6 carbon atoms.

The term "alkoxy" is used in the specification and claims to signify a moiety of the formula—OR", wherein R" is a straight or branched alkyl group containing from 1 to 4 carbon atoms.

The novel substituted spiropyrans of this invention are prepared by the acid-catalysed condensation of 4-alkoxy-2-hydroxybenzaldehyde with the appropriately substituted methyl ketone to form a styryl ketone intermediate which is not isolated. 2-Hydroxynaphthaldehyde is then added to the reaction mixture to thereby produce the desired substituted spiropyrans. Substantially equimolar amounts of the substituted methyl ketone, the 4-alkoxy-2-hydroxybenzaldehyde and the 2-Hydroxynaphthaldehyde are utilized in this process, which proceeds according to the following reaction formula:

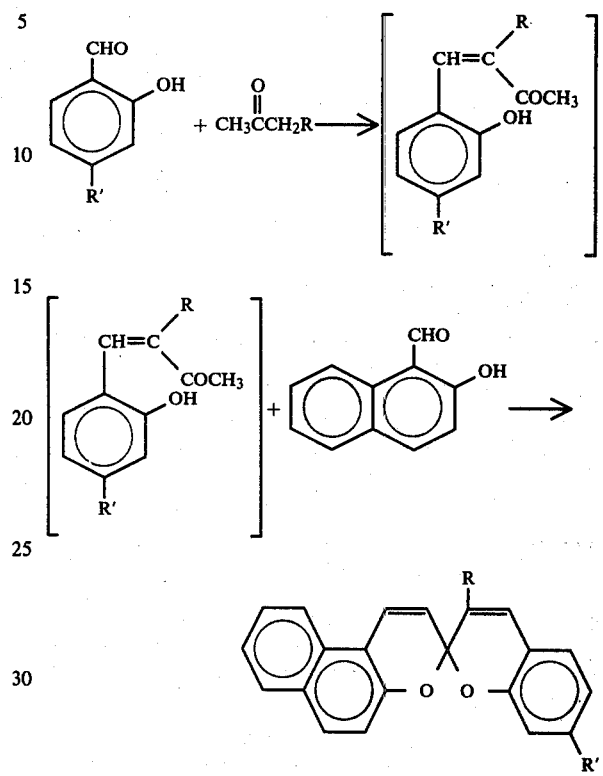

wherein R and R' are as defined above.

The 4-alkoxy-2-hydroxybenzaldehydes utilized herein can be prepared using the procedure as set forth in Collins et al., J. Chem. Soc. 1950 1876.

The substituted methyl ketones utilized herein are available commercially or can be prepared by using the procedures as set forth in *Organic Functional Group Preparation*, S. R. Sandler and W. Karo, Academic Press, New York, p. 169 and *Synthetic Organic Chemistry*, A. B. Wagner and H. D. Zook, New York, Wiley and Sons, Inc., p. 339.

The spiropyrans of this invention will react with photogenerated protic acids to form colored pyrilium salts. In this well-known method the protic acids, which are typically hydrogen halides, are generated by light within a substrate containing the spiropyran. Precursors for the hydrogen halides are typically trihalo alcohols, i.e. 2,2,2-tribromoethanol, which absorb light and generate hydrogen halides which react with the spiropyran to give a colored salt.

The stability of the colored pyrylium salts resulting from interaction of photogenerated protic acids with the spiropyrans is important. It is known that the nature of ring substitution (see rings A and B equation, below) can influence stability. (G. Arnold, G. Paal, and H. P. Vollmer, Z. Naturforsch. B 25 (12), 1413 (1970); U.S. Pat. No. 3,733,197 to C. Schiele.

Further it has now been found that substitution at the 7-position of ring B below of a π electron donating group is effective in stabilizing the color of pyrylium salts. The compounds of this invention have been found to be particularly effective in this respect.

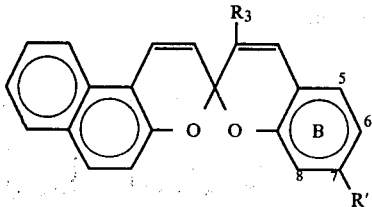

It has also been discovered that the spirobipyrans of this invention in which R is an unsaturated alkyl group, may be copolymerized with acrylates via a free radical process which utilizes well-known initiators such as, for example, 2,2'-azobis(2-methylpropionitrile) and azobis (isobutyronitrile). The resulting copolymers are precursors to chromogenic materials that find varied application from optical data storage to the formation of noncontact decorative patterns.

The term "acrylates" as used herein refers to acrylates and methacrylates that have the formula:

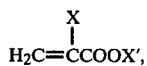

$$H_2C=CCOOX',$$

wherein X is H or $CH_3$ and X' is H or a straight or branched alkyl group having from 1 to 12 carbon atoms.

Reference is now made to the following examples which are provided to illustrate but not to limit the practice of this invention.

EXAMPLE B 1

Preparation of 3-Allyl-7-Methoxy-2,2'-Spiro-(2H-1-Benzopyran-2,3'-(3H)-Naphtho(2,1-b)Pyran)

Anhydrous hydrogen chloride was bubbled into a solution of 5-hexane-2-one (2.45 g, 0.025 mol) and 4-methoxy salicylaldehyde (3.8 g, 0.025 mol) in 15 ml of acetic acid cooled in an ice-water bath. The initially colorless solution turned deep magenta after 10–15 min. After ca. 1 hr the addition of hydrogen chloride was interrupted and 4.3 g (0.025 mol) of 2-hydroxyl naphthaldehyde in 20 ml of acetic acid was rapidly added to the reaction mixture. The addition of anhydrous hydrogen chloride was resumed. After ca. 1 hr the hydrogen chloride addition was stopped and the deep blue reaction mixture was stoppered and set aside at room temperature in the dark.

After ca. 4 days the viscous highly colored reaction mixture was diluted with 150 ml of ether and left to stand at room temperature. The mixture was filtered with suction and the highly colored irridescent gummy filter-cake was washed repeatedly with ether and dried in vacuo. The dried irridescent gum was suspended in 75 ml of actone and while cooling in an ice bath the mixture was made alkaline with dilute ammonium hydroxide. The gum dissolved and gave a magenta solution. The mixture was filtered with suction to remove a white solid (probably ammonium chloride) and the filtrate concentrated at reduced pressure. The residue was extracted with ether and the combined ether extracts was dried ove anhydrous magnesium sulfate.

The dried and filtered ethereal solution was concentrated at reduced pressure and left a deep magenta colored residue, 9.3 g (0.025 mol, 100%) of crude spirobipyran product. The crude product was chromatographed two times over Alumina (Fisher, A-540) using 50/50 (by volume) ethyl acetate and hexane as the eluent. The desired pure spiropyran product was recovered by concentration of the ethyl acetate-hexane solution at reduced pressure on the water aspirator, <40° and finally at <1 mm at room temperature. The product a pale green friable solid melted at 58°–63°. UV (THF) 236 nm (ε 64,835), 280 (18,680), 296 (17,580), 309 (16,480), 332 (6590), and 348 (6590). The NMR assignments for the product are summarized below.

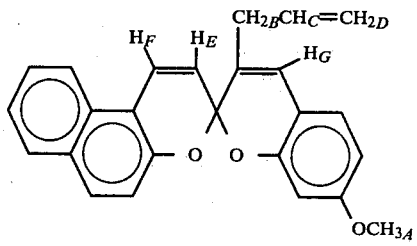

| Proton | $H_A$ | $H_B$ | $H_C$ | $H_D$ | $H_E$ | $H_F$ & $H_G$ | Aryl Protons |
|---|---|---|---|---|---|---|---|
| Chemical* Shifts, ppm, | 3.60 (s) | 3.2 (d) | 5.9 (m) | 5.13 (m) | 6.08 (d) | in aromatic region | 6.2–8.3 |

*In $CDCl_3$ solvent, TMS as internal standard.

EXAMPLE 2

Copolymerization of Methyl Methacrylate with 3-Allyl-7-Methoxy-2,2'-Spiro(2H-1-Benzopyran-2,3'-(3H)-Naphtho(2,1-b)Pyran)

Methyl methacrylate (15 g, 0.15 mol) and the product of Example 1 (0.75 g, 0.002 mol) along with 0.045 g of azobisisobutyronitrile initiator were charged into a pyrex glass pressure tube (ca. 70 ml capacity). The resulting clear pale yellow solution was given a subsurface purge with nitrogen for 30 min and sealed. The air-tight tube was placed in a water bath maintained at 70° C. for ca. 8 hrs. After cooling to room temperature, the glass pressure tube was opened and the copolymer (a glass-like rod) was removed. The copolymer was reprecipitated from ethyl acetate (8.2% solution) by addition to excess hexane and dried in vacuo.

A UV spectrum of a 0.1-0.2 mil film cast from ethyl acetate showed the following λ max: 275, 296, 308, and 346 nm.

What is claimed is:

1. A spiropyran compound having the formula

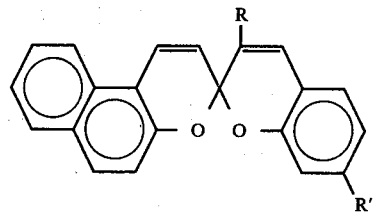

wherein R represents alkylene aryl, aryl, unsaturated alkyl or cycloalkyl and R' is alkoxy.

2. The compound of claim 1 wherein R is unsaturated alkyl.

3. The compound of claim 2 which is 3-allyl-7-methoxy-2,2'-spiro(2H-1-benzopyran-2,3'-(3H)-naphtho(2,1-b)pyran).

4. A copolymer produced by the free radical polymerization of a spiropyran compound of claim 2 and an acryate of the formula
wherein X is H or CH₃ and X' is H or a straight or branched alkyl group having from 1 to 12 carbon atoms.
* * * * *